US012123852B1

(12) United States Patent
Hu et al.

(10) Patent No.: US 12,123,852 B1
(45) Date of Patent: Oct. 22, 2024

(54) MULTIFUNCTIONAL AND VISUAL ROCK TRIAXIAL TESTING SYSTEM

(71) Applicant: INSTITUTE OF GEOLOGY AND GEOPHYSICS, CHINESE ACADEMY OF SCIENCES, Beijing (CN)

(72) Inventors: Yanzhi Hu, Beijing (CN); Xiao Li, Beijing (CN); Tianqiao Mao, Beijing (CN); Shouding Li, Beijing (CN); Jianming He, Beijing (CN); Zhaobin Zhang, Beijing (CN); Guanfang Li, Beijing (CN); Bo Zheng, Beijing (CN)

(73) Assignee: INSTITUTE OF GEOLOGY AND GEOPHYSICS, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 18/668,177

(22) Filed: May 19, 2024

(30) Foreign Application Priority Data

Jun. 29, 2023 (CN) .......................... 202310778313.9

(51) Int. Cl.
*G01N 3/12* (2006.01)
*G01N 23/046* (2018.01)
*G01N 33/24* (2006.01)

(52) U.S. Cl.
CPC .............. *G01N 3/12* (2013.01); *G01N 33/24* (2013.01); *G01N 23/046* (2013.01); *G01N 2203/0003* (2013.01); *G01N 2203/0019* (2013.01); *G01N 2203/0048* (2013.01); *G01N 2203/0256* (2013.01); *G01N 2223/419* (2013.01)

(58) Field of Classification Search
CPC ........ G01N 3/12; G01N 33/24; G01N 23/046; G01N 2203/0003; G01N 2203/0019; G01N 2203/0048; G01N 2203/0256; G01N 2223/419
See application file for complete search history.

(56) References Cited

U.S. PATENT DOCUMENTS 10,139,355 B1 * 11/2018 Li ........................ G01N 23/046
10,948,431 B1 * 3/2021 Zheng .................... G01N 33/24

FOREIGN PATENT DOCUMENTS

| AU | 2020101248 A4 | 8/2020 | |
| CN | 107462190 A | 12/2017 | |
| CN | 109580365 A * | 4/2019 | ............. G01N 23/04 |

(Continued)

*Primary Examiner* — Shelby A Turner
*Assistant Examiner* — Yaritza H Perez Bermudez
(74) *Attorney, Agent, or Firm* — Bayramoglu Law Offices LLC (57) ABSTRACT

A multifunctional and visual rock triaxial testing system is provided. The multifunctional and visual rock triaxial testing system includes an axial loading system, a high-energy accelerator computerized tomography (CT) scanning system, a turntable system, a triaxial pressure cell, a fluid fracturing pump, a temperature pump, a confining pressure loading pump, a power oil source, and an integrated control console, where the turntable system is configured to drive the high-energy accelerator CT scanning system to rotate, so as to scan an internal structure of a rock sample; and the triaxial pressure cell and the fluid fracturing pump are configured to conduct compression and fracturing tests on the rock sample, respectively.

8 Claims, 9 Drawing Sheets

(56) References Cited

FOREIGN PATENT DOCUMENTS

| CN | 108801799 B | * | 2/2020 | ............... G01N 3/12 |
| CN | 111157557 A | * | 5/2020 | ........... G01N 23/046 |
| CN | 111238973 A | * | 6/2020 | ............... G01N 3/02 |
| CN | 112255112 A |   | 1/2021 | |
| CN | 115773954 A |   | 3/2023 | |

* cited by examiner

MULTIFUNCTIONAL AND VISUAL ROCK TRIAXIAL TESTING SYSTEM

CROSS-REFERENCE TO THE RELATED APPLICATIONS

This application is based upon and claims priority to Chinese Patent Application No. 202310778313.9, filed on Jun. 29, 2023, the entire contents of which are incorporated herein by reference.

TECHNICAL FIELD

The present disclosure belongs to the field of rock mechanics tests and devices for rock mechanics tests, and in particular to a multifunctional and visual rock triaxial testing system.

BACKGROUND

Rock fracture is common in rock engineering. From earthquakes to rock engineering instability, each are related to rock fracture. That is why it is needed to study rock fracture. Some projects, such as reservoir dams, landslide control, and tunnel construction, require prevention, prediction, and reinforcement of rock fracture. Once rock fracture occurs, it may cause huge economic losses and casualties. Some projects require artificial fracturing of rocks. For example, unconventional reservoirs such as shale gas reservoirs must undergo hydraulic fracturing to achieve industrial production capacity. Therefore, studying the formation and evolution process of rock fracture under the action of in-situ stress, temperature, and fluid has important engineering and scientific significance.

In-situ computerized tomography (CT) scanning technology provides an important means for the realization of this process. Experts and scholars worldwide have conducted numerous studies on CT scanning-based in-situ rock mechanics testing systems and achieved a series of results. However, the CT scanning-based in-situ rock mechanics triaxial testing systems have certain shortcomings. 1) The radiation energy of traditional industrial CT and medical CT is not enough to penetrate the rock sample and counterforce device, 2) the resolution of the CT scanning system is low, 3) the rock loading device usually uses a pressure cell as a reaction frame, resulting in insufficient overall rigidity of the testing system and making it hard to acquire the post-peak curve of rock compression deformation, especially for hard rock, 4) due to the limitation of CT imaging principle, the imaging object needs to rotate 360-degree relative to the CT radiation source and detector, causing entanglement in the high-pressure line, circuit, and signal line of the rock triaxial testing system.

Chinese Patent Application CN201811224053.6 provides a high-energy accelerator CT-based rock mechanics testing system. In this disclosure, the innovative use of high-energy accelerator CT solves the problem of low CT radiation energy and resolution. Four columns form a reaction frame, solving the problem of insufficient rigidity in the testing system. A rotating slip ring for power supply and liquid supply is used to solve the entanglement problem in the high-pressure line, wire, and signal line during CT imaging. However, this disclosure has problems with complex structure and control system, as well as large overall volume. In addition, due to the dynamic variation of the test force applied during the loading process, the testing system requires high response speed for the control system.

In view of this, the present disclosure provides a multifunctional and visual rock triaxial testing system.

SUMMARY

The present disclosure aims to solve the above problems of testing systems in the prior art, such as the insufficient overall rigidity, the low resolution of the CT scanning system, the complex structure of the control system, the large overall volume, and the entanglement problem in the high-pressure line, the circuit, and the signal line. To this end, the present disclosure provides a multifunctional and visual rock triaxial testing system.

The multifunctional and visual rock triaxial testing system includes an axial loading system, a high-energy accelerator CT scanning system, a turntable system, a triaxial pressure cell, a fluid fracturing pump, a temperature pump, a confining pressure loading pump, a power oil source, and an integrated control console, where the axial loading system is fixed to a ground and configured to provide an axial stress for rock compression and fracturing tests; the high-energy accelerator CT scanning system is provided inside the axial loading system and configured to perform real-time scanning on an internal structure of a rock; the turntable system is provided between the axial loading system and the high-energy accelerator CT scanning system and rotationally connected to the high-energy accelerator CT scanning system; and the triaxial pressure cell is provided inside the high-energy accelerator CT scanning system and configured to simulate a true formation temperature, stress, and fluid environment in which the rock is located; and the fluid fracturing pump is fixed to the ground, connected to the triaxial pressure cell, and configured to conduct a fluid fracturing test; the temperature pump is fixed to the ground, connected to the triaxial pressure cell, and configured to provide a true temperature field for the rock; the confining pressure loading pump is fixed to the ground and configured to provide a true stress field for the rock; the power oil source is fixed to the ground and configured to provide power for the axial loading system, the confining pressure loading pump, and the fluid fracturing pump; and the integrated control console is configured to control the axial loading system, the high-energy accelerator CT scanning system, the turntable system, the triaxial pressure cell, the fluid fracturing pump, the temperature pump, the confining pressure loading pump, and the power oil source, and acquire data in real time.

In some preferred implementations, the axial loading system includes a reaction frame, an axial loading cylinder body, an axial loading cylinder connecting flange, an axial loading cylinder piston, and an axial loading cylinder platform; and the reaction frame is fixed to the ground and the axial loading cylinder body; the axial loading cylinder piston is located in the axial loading cylinder body and moves along the axial loading cylinder body; the axial loading cylinder piston is connected to the axial loading cylinder body through the axial loading cylinder connecting flange in a moving and sealed manner; the axial loading cylinder piston is fixed to the axial loading cylinder platform; and the axial loading cylinder platform is fixed to the triaxial pressure cell.

In some preferred implementations, the high-energy accelerator CT scanning system includes a detector bracket, a detector lifting system, a detector, a radiation source bracket, a radiation source lifting system, a radiation source, and a CT line assembly;

the detector bracket is connected to the turntable system and fixed to the detector lifting system; the detector lifting system is fixed to the detector; and the detector is configured to image the internal structure of the rock;

the radiation source bracket is connected to the turntable system and fixed to the radiation source lifting system; the radiation source lifting system is fixed to the radiation source; and the radiation source is configured to emit an X-ray to the rock; and the CT line assembly is connected to the turntable system and configured to control the high-energy accelerator CT scanning system.

In some preferred implementations, the turntable system includes a turntable rotor, a turntable stator, and a rotating tow;

the turntable rotor is fixed to the detector bracket, the radiation source bracket, and the CT line assembly; the turntable rotor is connected to the turntable stator through a bearing; and the turntable stator is fixed to the reaction frame; and one end of the rotating tow is fixed to the turntable rotor, and the rotating tow is able to coil around the turntable stator; the CT line assembly is located in the rotating tow; and the rotating tow is configured to pull the CT line assembly.

In some preferred implementations, the triaxial pressure cell includes a pressure cell base, a pressure cell cylinder body, a pressure cell end cap, a pressure cell piston, a rock sample assembly device, a high-low temperature heat exchange tube, a built-in pressure sensor, and a ball-and-socket device;

the pressure cell base is detachably fixed to the axial loading cylinder platform and fixed to a lower surface of the pressure cell cylinder body; the pressure cell cylinder body is provided therein with the rock sample assembly device; and a lower surface of the rock sample assembly device is fixed to the pressure cell base;

the high-low temperature heat exchange tube is located between the rock sample assembly device and an inner surface of the pressure cell cylinder body; and the high-low temperature heat exchange tube is fixed to the inner surface of the pressure cell cylinder body and rigidly connected to the temperature pump through a through-hole in the pressure cell base; and an upper surface of the rock sample assembly device is fixed to the ball-and-socket device; the ball-and-socket device is fixed to the built-in pressure sensor; the built-in pressure sensor is fixed to the pressure cell piston; the pressure cell piston is movable along an inner surface of the pressure cell end cap; the pressure cell end cap is fixed to an upper surface of the pressure cell cylinder body; and the pressure cell piston is fixed to the reaction frame.

In some preferred implementations, the rock sample assembly device includes a lower compression test pad, an axial deformation sensor, a radial deformation sensor, a compression test rock sample, an axial deformation cone, a contact bolt, and an upper compression test pad;

the lower compression test pad is fixed to the pressure cell base and the axial deformation sensor; the axial deformation sensor is butted with the axial deformation cone; the axial deformation cone is fixed to the upper compression test pad; the upper compression test pad is connected to the ball-and-socket device; and the compression test rock sample is located in the axial deformation sensor and butted with the axial deformation cone; and the lower compression test pad is fixed to the radial deformation sensor; the radial deformation sensor is fixed to the contact bolt; and the contact bolt is butted with the compression test rock sample.

In another variation of the present disclosure, the rock sample assembly device includes the axial deformation sensor, the radial deformation sensor, the axial deformation cone, the contact bolt, a lower fracturing test pad, a fracturing test rock sample, and an upper fracturing test pad;

the lower fracturing test pad is fixed to the pressure cell base and the axial deformation sensor; the axial deformation sensor is butted with the axial deformation cone; the axial deformation cone is fixed to the upper fracturing test pad; the upper fracturing test pad is connected to the ball-and-socket device; and the fracturing test rock sample is located in the axial deformation sensor and butted with the axial deformation cone;

the lower fracturing test pad is fixed to the radial deformation sensor; the radial deformation sensor is fixed to the contact bolt; and the contact bolt is butted with the fracturing test rock sample; and a center of the lower fracturing test pad is provided with a fluid injection hole and rigidly connected to the fluid fracturing pump through a hole in the pressure cell base.

In some preferred implementations, the axial deformation sensor and the radial deformation sensor are provided with an elastic rod structure and measure a deformation by a strain gauge on an elastic rod.

In some preferred implementations, the reaction frame is configured to carry a reaction force during axial loading.

In some preferred implementations, the CT line assembly includes CT electrical, optical, and control signals.

The present disclosure has following beneficial effects:

The present disclosure overcomes the problems in existing equipment, such as low radiation energy, low resolution, low rigidity of the loading reaction frame, and line entanglement during the testing process. The present disclosure has the advantages of low cost, simple structure, simple control system, collectable post-peak curve (especially for hard rock), and visible whole testing process. The present disclosure can achieve compressive deformation tests and fracturing tests of rocks under the combined effects of temperature, stress, and fluid, and can achieve real-time visualization of the testing process. Therefore, the present disclosure provides an important technical means for opening the "black box" of rock fracture processes.

BRIEF DESCRIPTION OF THE DRAWINGS

Other features, objectives and advantages of the present disclosure will become more apparent upon reading the detailed description of the non-restrictive embodiments with reference to the following drawings.

DETAILED DESCRIPTION OF THE EMBODIMENTS

The present disclosure will be further described in detail below with reference to the drawings and embodiments. It should be understood that the specific embodiments described herein are merely intended to explain the present disclosure, rather than to limit the present disclosure. It should also be noted that, for convenience of description, only the parts related to the present disclosure are shown in the accompanying drawings.

It should be noted that the embodiments in the present disclosure and features in the embodiments may be combined with each other in a non-conflicting situation. The present disclosure will be described in detail below with reference to the drawings and embodiments.

Figure 1:
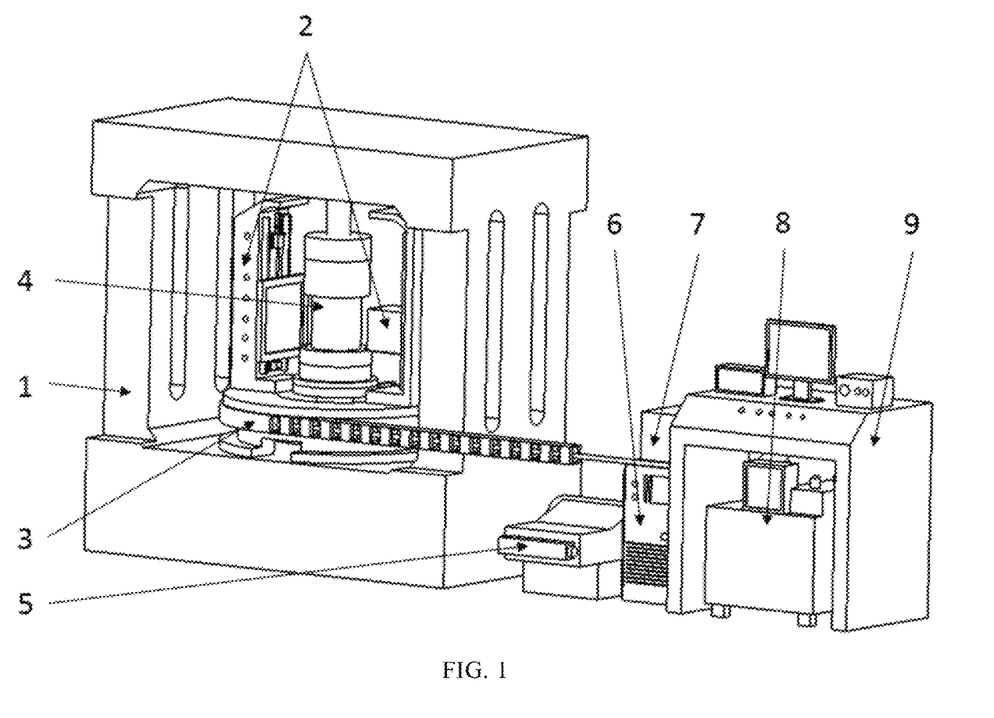
FIG. 1 is an isometric diagram of a multifunctional and visual rock triaxial testing system according to the present disclosure.
Figure 2:
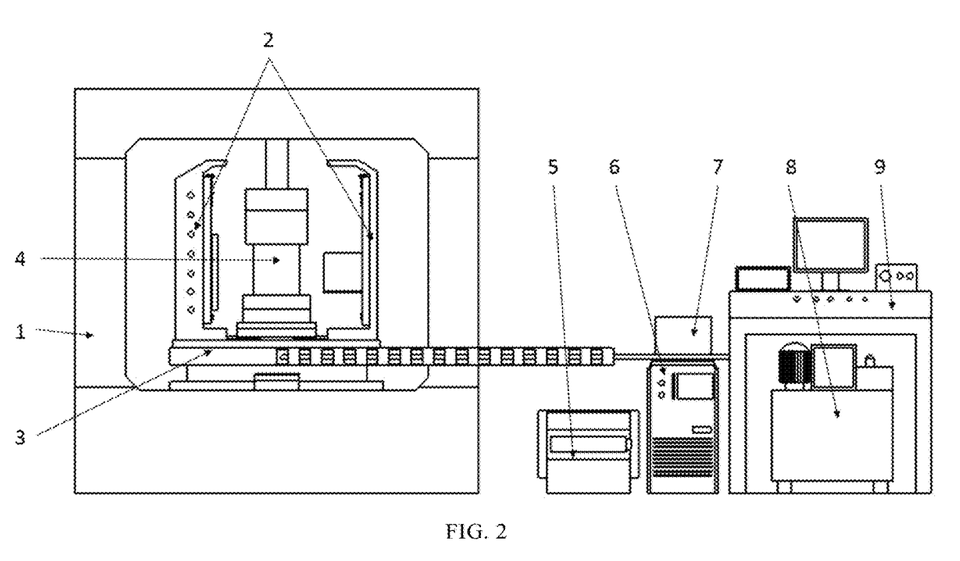
FIG. 2 is a front view of the multifunctional and visual rock triaxial testing system according to the present disclosure.

As shown in FIGS. 1 to 9, the present disclosure provides a multifunctional and visual rock triaxial testing system. Referring to FIGS. 1 and 2, the testing system includes axial loading system 1, high-energy accelerator CT scanning system 2, turntable system 3, triaxial pressure cell 4, fluid fracturing pump 5, temperature pump 6, confining pressure loading pump 7, power oil source 8, and integrated control console 9.

The axial loading system 1 is fixed to a ground and configured to provide an axial stress for rock compression and fracturing tests. The high-energy accelerator CT scanning system 2 is provided inside the axial loading system 1 and configured to perform real-time scanning on an internal structure of a rock. The turntable system 3 is provided between the axial loading system 1 and the high-energy accelerator CT scanning system 2 and rotationally connected to the high-energy accelerator CT scanning system 2. The triaxial pressure cell 4 is provided inside the high-energy accelerator CT scanning system 2 and configured to simulate a true formation temperature, stress, and fluid environment in which the rock is located.

The fluid fracturing pump 5 is fixed to the ground, connected to the triaxial pressure cell 4, and configured to conduct a fluid fracturing test. The temperature pump 6 is fixed to the ground, connected to the triaxial pressure cell 4, and configured to provide a true temperature field for the rock. The confining pressure loading pump 7 is fixed to the ground and configured to provide a true stress field for the rock. The power oil source 8 is fixed to the ground and configured to provide power for the axial loading system 1, the confining pressure loading pump 7, and the fluid fracturing pump 5. The integrated control console 9 is configured to control the axial loading system 1, the high-energy accelerator CT scanning system 2, the turntable system 3, the triaxial pressure cell 4, the fluid fracturing pump 5, the temperature pump 6, the confining pressure loading pump 7, and the power oil source 8, and acquire data in real time.

The rock includes compression test rock sample 4.5.4 and fracturing test rock sample 4.5.9.

The fluid fracturing pump 5 is configured to inject a high-pressure fluid to simulate hydraulic fracturing, carbon dioxide fracturing, etc. in energy exploration.

Figure 5:
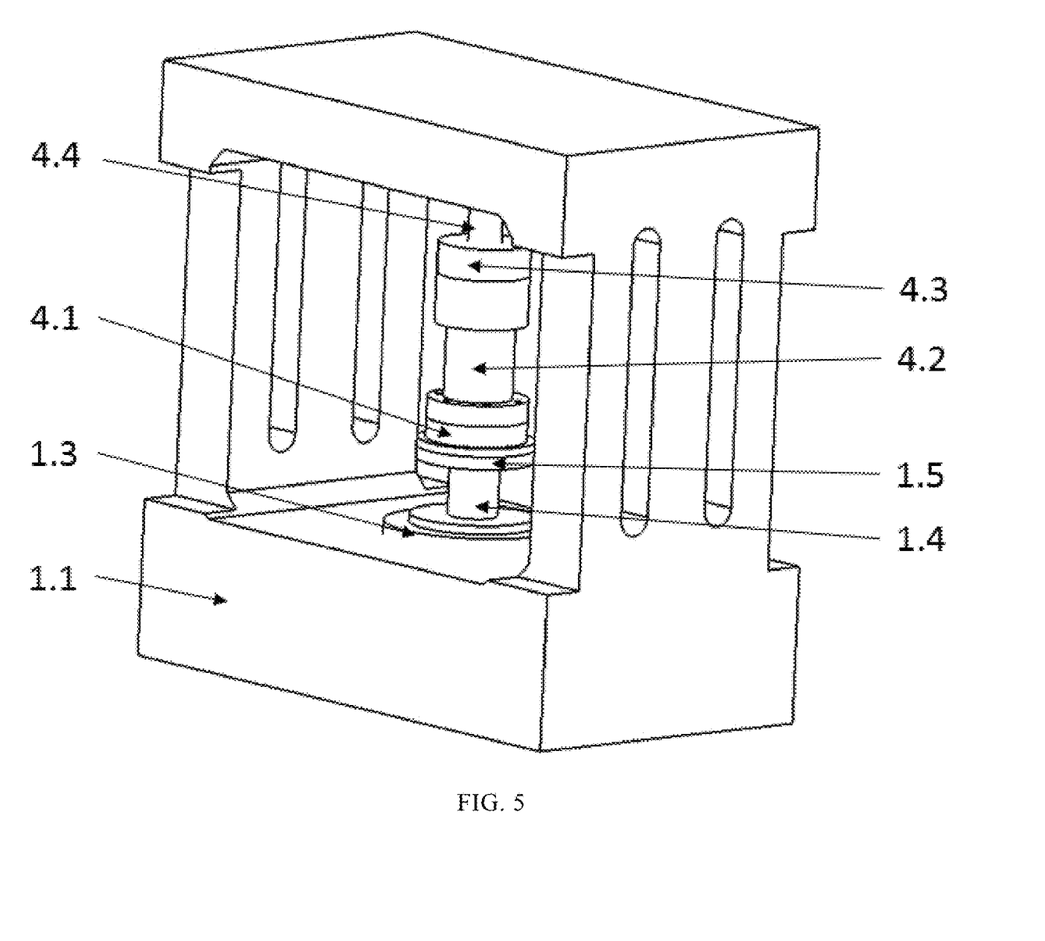
FIG. 5 is an isometric diagram of an axial loading system and a triaxial pressure cell of the multifunctional and visual rock triaxial testing system according to the present disclosure.
Figure 6:
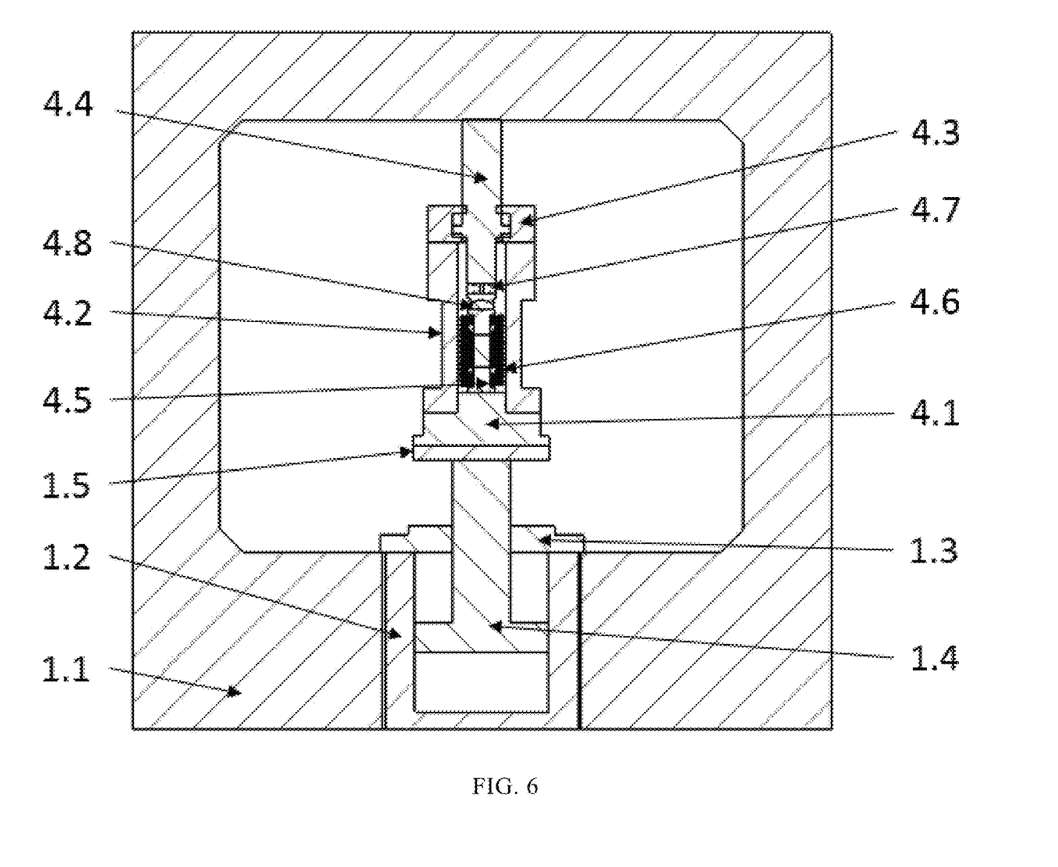
FIG. 6 is a section view of the axial loading system and the triaxial pressure cell of the multifunctional and visual rock triaxial testing system according to the present disclosure.

Preferably, referring to FIGS. 5 and 6, the axial loading system 1 includes reaction frame 1.1, axial loading cylinder body 1.2, axial loading cylinder connecting flange 1.3, axial loading cylinder piston 1.4, and axial loading cylinder platform 1.5.

The reaction frame 1.1 is fixed to the ground and the axial loading cylinder body 1.2. The axial loading cylinder piston 1.4 is located in the axial loading cylinder body 1.2 and moves along the axial loading cylinder body. The axial loading cylinder piston 1.4 is connected to the axial loading cylinder body 1.2 through the axial loading cylinder connecting flange 1.3 in a moving and sealed manner. The axial loading cylinder piston 1.4 is fixed to the axial loading cylinder platform 1.5. The axial loading cylinder platform 1.5 is fixed to the triaxial pressure cell 4.

The reaction frame 1.1 is a high-rigidity loading reaction frame with high overall rigidity and small deformation, avoiding the low rigidity problem in existing equipment that uses a pressure cell as a reaction frame.

Figure 3:
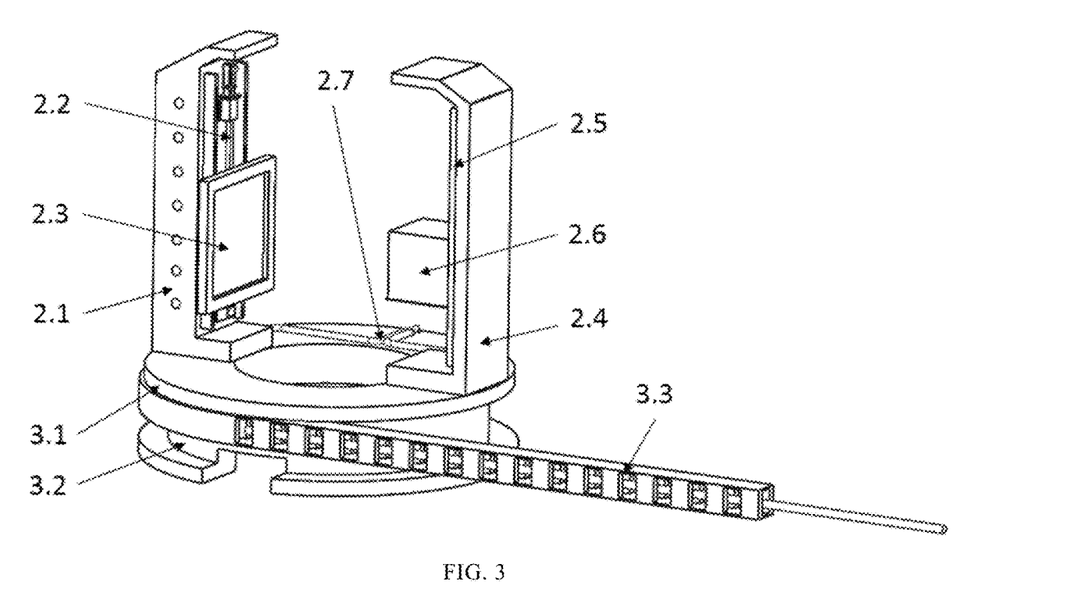
FIG. 3 is an isometric diagram of a high-energy accelerator CT scanning system and a turntable system of the multifunctional and visual rock triaxial testing system according to the present disclosure.
Figure 4:
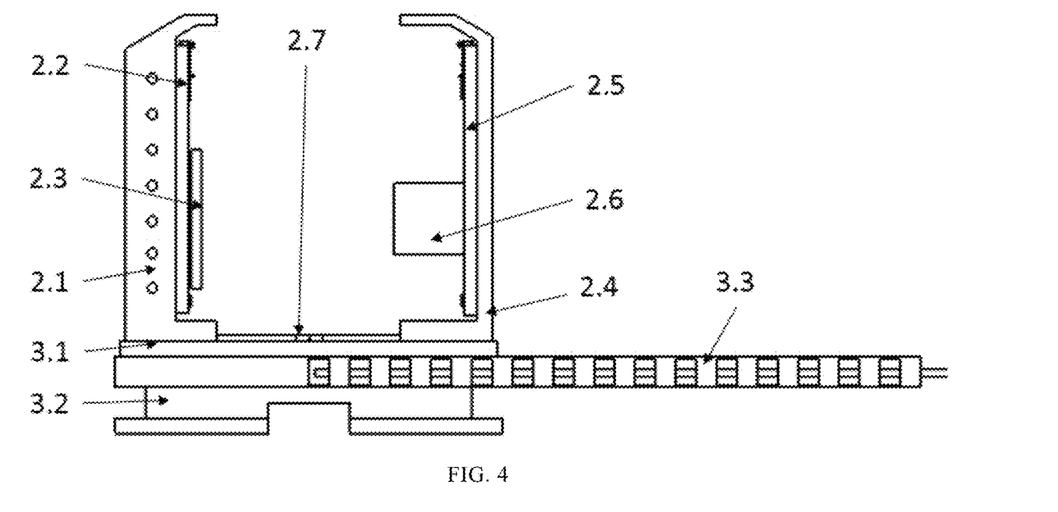
FIG. 4 is a front view of the high-energy accelerator CT scanning system and the turntable system of the multifunctional and visual rock triaxial testing system according to the present disclosure.

Preferably, referring to FIGS. 2, 3, and 4, the high-energy accelerator CT scanning system 2 includes detector bracket 2.1, detector lifting system 2.2, detector 2.3, radiation source bracket 2.4, radiation source lifting system 2.5, radiation source 2.6, and CT line assembly 2.7.

The detector bracket 2.1 is connected to the turntable system 3 and fixed to the detector lifting system 2.2. The detector lifting system 2.2 is fixed to the detector 2.3. The detector 2.3 is configured to image the internal structure of the rock.

The radiation source bracket 2.4 is connected to the turntable system 3 and fixed to the radiation source lifting system 2.5. The radiation source lifting system 2.5 is fixed to the radiation source 2.6. The radiation source 2.6 is configured to emit an X-ray to the rock.

The CT line assembly 2.7 is connected to the turntable system 3 and configured to control the high-energy accelerator CT scanning system 2.

Preferably, referring to FIGS. 3 and 4, the turntable system 3 includes turntable rotor 3.1, turntable stator 3.2, and rotating tow 3.3.

The turntable rotor 3.1 is fixed to the detector bracket 2.1, the radiation source bracket 2.4, and the CT line assembly 2.7. The turntable rotor 3.1 is connected to the turntable stator 3.2 through a bearing. The turntable stator 3.2 is fixed to the reaction frame 1.1.

One end of the rotating tow 3.3 is fixed to the turntable rotor 3.1, and the rotating tow 3.3 is able to coil around the turntable stator 3.2. The CT line assembly 2.7 is located in the rotating tow 3.3, and the rotating tow 3.3 is configured to pull the CT line assembly 2.7.

The detector 2.3 is configured to detect an attenuation of the X-ray after the X-ray passes through an object.

The detector lifting system 2.2 and the radiation source lifting system 2.5 are configured to adjust an imaging position so as to ensure that the rock sample is within an imaging range.

Preferably, referring to FIGS. 2, 5, 6, and 7, the triaxial pressure cell 4 includes pressure cell base 4.1, pressure cell cylinder body 4.2, pressure cell end cap 4.3, pressure cell piston 4.4, rock sample assembly device 4.5, high-low temperature heat exchange tube 4.6, built-in pressure sensor 4.7, and ball-and-socket device 4.8.

The pressure cell base 4.1 is detachably fixed to the axial loading cylinder platform 1.5 and fixed to a lower surface of the pressure cell cylinder body 4.2. The pressure cell cylinder body 4.2 is provided therein with the rock sample assembly device 4.5. A lower surface of the rock sample assembly device 4.5 is fixed to the pressure cell base 4.1.

The high-low temperature heat exchange tube 4.6 is located between the rock sample assembly device 4.5 and an inner surface of the pressure cell cylinder body 4.2. The high-low temperature heat exchange tube 4.6 is fixed to the inner surface of the pressure cell cylinder body 4.2 and rigidly connected to the temperature pump 6 through a through-hole in the pressure cell base 4.1.

An upper surface of the rock sample assembly device 4.5 is fixed to the ball-and-socket device 4.8. The ball-and-socket device 4.8 is fixed to the built-in pressure sensor 4.7. The built-in pressure sensor 4.7 is fixed to the pressure cell piston 4.4. The pressure cell piston 4.4 is movable along an inner surface of the pressure cell end cap 4.3. The pressure cell end cap 4.3 is fixed to an upper surface of the pressure cell cylinder body 4.2. The pressure cell piston 4.4 is fixed to the reaction frame 1.1.

The above content is designed for a compression test.

Figure 7:
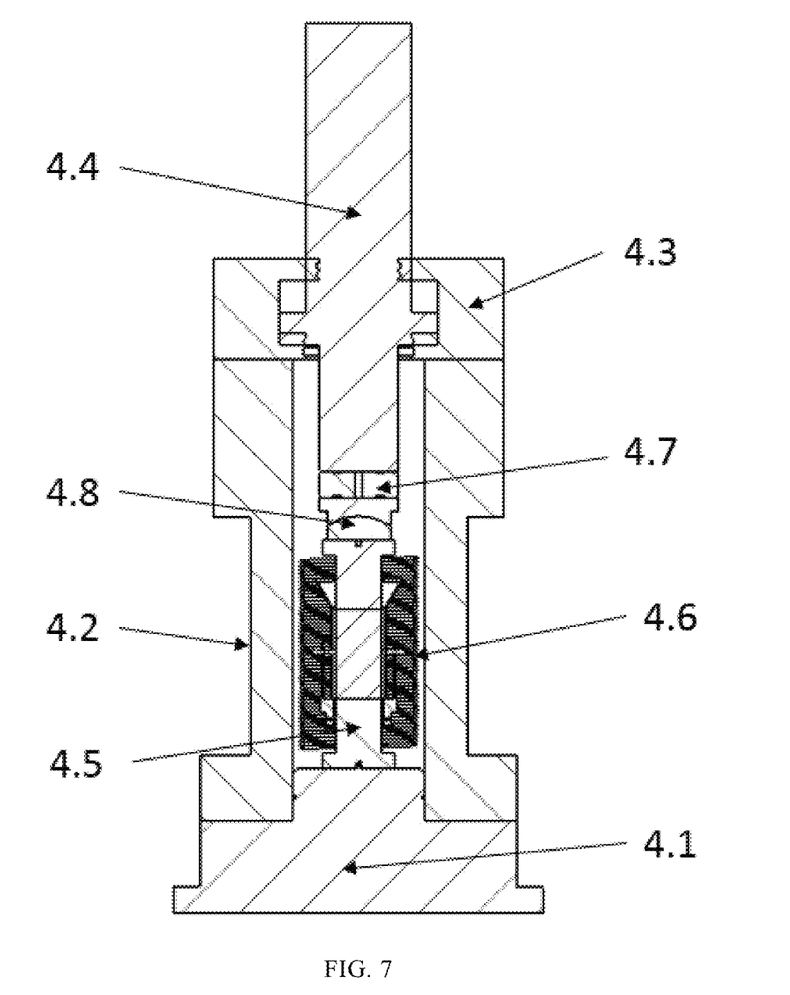
FIG. 7 is a section view of the triaxial pressure cell 4 of the multifunctional and visual rock triaxial testing system according to the present disclosure.

The high-low temperature heat exchange tube 4.6 is configured to circulate heat exchange.

Through the built-in pressure sensor 4.7, the present disclosure overcomes the problem that a traditional external measurement result is affected by friction between a piston and the pressure cell end cap 4.3, and achieves accurate axial force measurement. The ball-and-socket device 4.8 is configured to ensure that an axial force is perpendicular to upper and lower sections of the rock, avoiding local stress concentration caused by uneven processing of the rock sample section.

Figure 8:
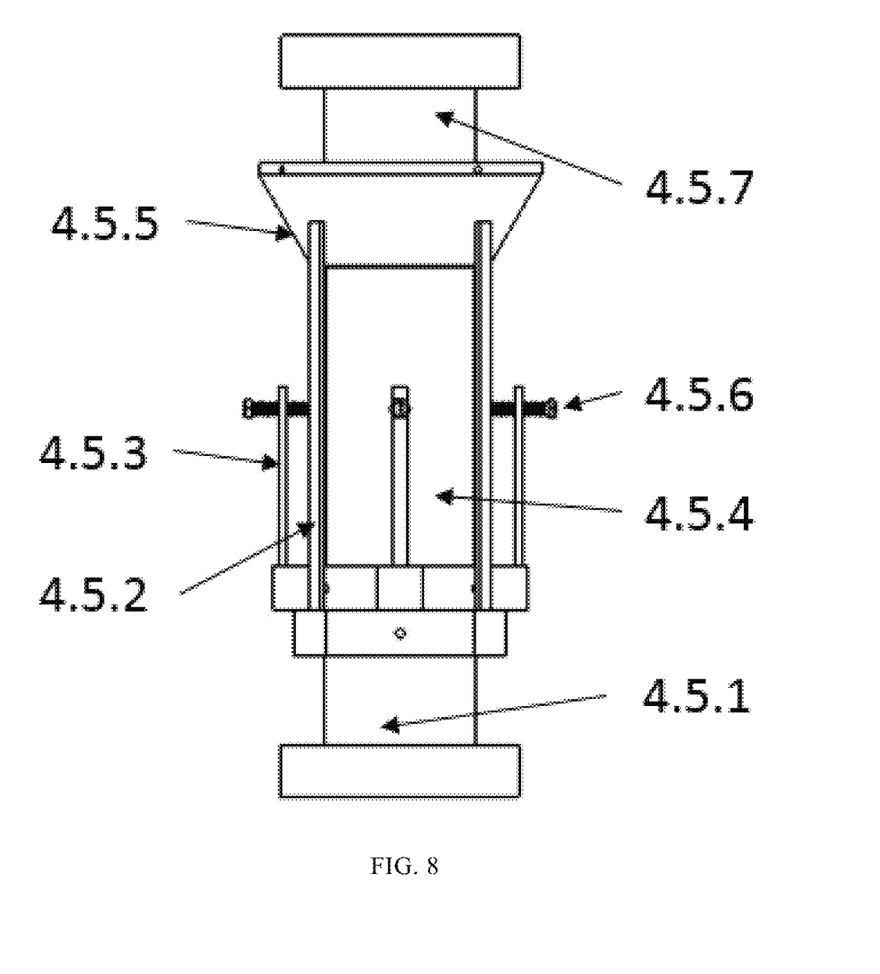
FIG. 8 is an assembly diagram of the multifunctional and visual rock triaxial testing system for a rock sample compression test according to the present disclosure.

Preferably, referring to FIGS. 6, 7, and 8, the rock sample assembly device 4.5 includes lower compression test pad 4.5.1, axial deformation sensor 4.5.2, radial deformation sensor 4.5.3, the compression test rock sample 4.5.4, axial deformation cone 4.5.5, contact bolt 4.5.6, and upper compression test pad 4.5.7.

The lower compression test pad 4.5.1 is fixed to the pressure cell base 4.1 and the axial deformation sensor 4.5.2. The axial deformation sensor 4.5.2 is butted with the axial deformation cone 4.5.5. The axial deformation cone 4.5.5 is fixed to the upper compression test pad 4.5.7. The upper compression test pad 4.5.7 is connected to the ball-and-socket device 4.8. The compression test rock sample 4.5.4 is located in the axial deformation sensor 4.5.2 and butted with the axial deformation cone 4.5.5.

The lower compression test pad 4.5.1 is fixed to the radial deformation sensor 4.5.3. The radial deformation sensor 4.5.3 is fixed to the contact bolt 4.5.6. The contact bolt 4.5.6 is butted with the compression test rock sample 4.5.4.

The upper compression test pad 4.5.7 is fixed to the ball-and-socket device 4.8.

During a loading process, the axial deformation cone 4.5.5 moves along with the upper compression test pad 4.5.7 and moves relative to the axial deformation sensor 4.5.2. In this way, four elastic rods of the axial deformation sensor 4.5.2 are spread out by a conical surface, and the deformation of the compression test rock sample 4.5.4 is measured by a strain gauge attached to the elastic rod. The compression test rock sample 4.5.4 undergoes radial deformation and expansion. Four elastic rods of the radial sensor are driven by the contact bolt 4.5.6 to undergo axial deformation, and the radial deformation of the rock is measured by a strain gauge attached to the elastic rod.

Figure 9:
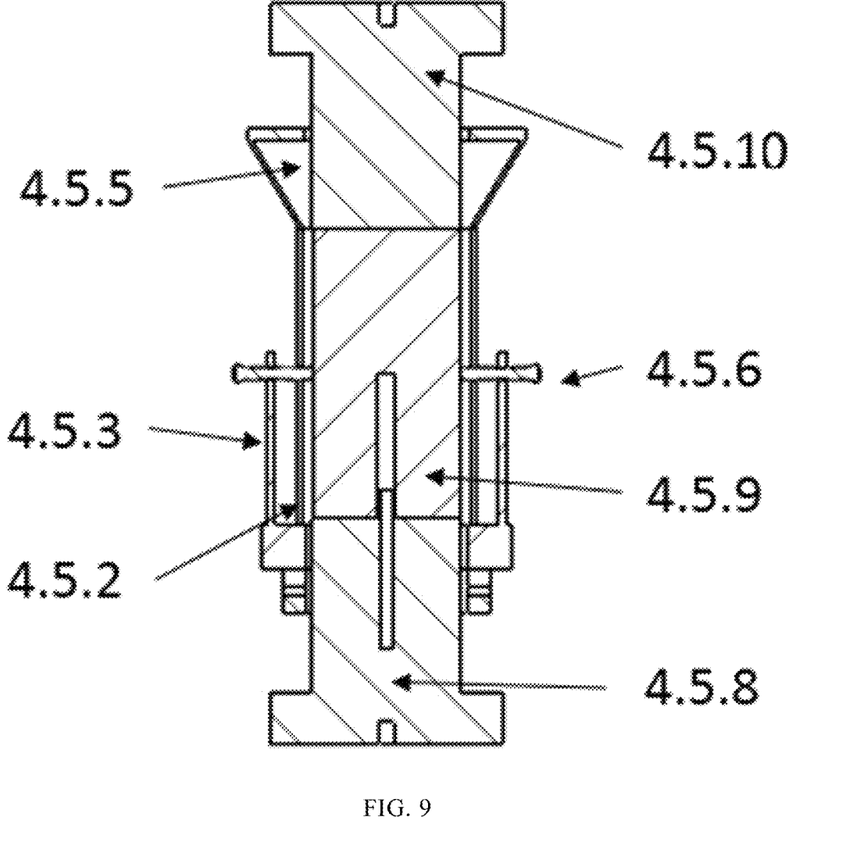
FIG. 9 is an assembly diagram of the multifunctional and visual rock triaxial testing system for a rock sample fracturing test according to the present disclosure.

Preferably, referring to FIGS. 6, 7, and 9, in another variation of the present disclosure, the rock sample assembly device 4.5 includes the axial deformation sensor 4.5.2, the radial deformation sensor 4.5.3, the axial deformation cone 4.5.5, the contact bolt 4.5.6, lower fracturing test pad 4.5.8, the fracturing test rock sample 4.5.9, and upper fracturing test pad 4.5.10.

The lower fracturing test pad 4.5.8 is fixed to the pressure cell base 4.1 and the axial deformation sensor 4.5.2. The axial deformation sensor 4.5.2 is butted with the axial deformation cone 4.5.5. The axial deformation cone 4.5.5 is fixed to the upper fracturing test pad 4.5.10. The upper fracturing test pad 4.5.10 is connected to the ball-and-socket device 4.8. The fracturing test rock sample 4.5.9 is located in the axial deformation sensor 4.5.2 and butted with the axial deformation cone 4.5.5.

The lower fracturing test pad 4.5.8 is fixed to the radial deformation sensor 4.5.3. The radial deformation sensor 4.5.3 is fixed to the contact bolt 4.5.6. The contact bolt 4.5.6 is butted with the fracturing test rock sample 4.5.9.

A center of the lower fracturing test pad 4.5.8 is provided with a fluid injection hole and rigidly connected to the fluid fracturing pump 5 through a hole in the pressure cell base 4.1.

The upper fracturing test pad 4.5.10 is fixed to the ball-and-socket device 4.8.

The above content is designed for a fracturing test.

The center of the lower fracturing test pad 4.5.8 is provided with the fluid injection hole, which is rigidly connected to the fluid fracturing pump 5 through the hole in the pressure cell base 4.1, allowing for the fluid fracturing test to be conducted. A center of the fracturing test rock sample is provided with a hole that reaches half a height of the sample to simulate perforation during fluid fracturing.

Preferably, referring to FIGS. 8 and 9, the axial deformation sensor 4.5.2 and the radial deformation sensor 4.5.3 are provided with an elastic rod structure and measure a deformation by a strain gauge on the elastic rod.

Preferably, referring to FIG. 5, the reaction frame 1.1 is configured to carry a reaction force during axial loading.

Preferably, referring to FIGS. 3 and 4, the CT line assembly 2.7 includes CT electrical, optical, and control signals.

As shown in FIGS. 1 to 9, a second embodiment of the present disclosure provides a multifunctional and visual rock triaxial testing method, which is based on the fracturing test of the multifunctional and visual rock triaxial testing system, and includes the following steps.

S1. The processed fracturing test rock sample 4.5.9 is provided with the hole with a depth of half the height of the rock sample.

S2. The lower fracturing test pad 4.5.8 is bonded with the fracturing test rock sample 4.5.9 through high-strength glue, and curing is conducted for 24 h to ensure a sufficient bonding strength.

S3. The triaxial pressure cell 4 is removed from a middle position of the high-energy accelerator CT scanning system 2, and background CT scanning is conducted to acquire a background image.

S4. The bonded fracturing test rock sample 4.5.9 and the upper fracturing test pad 4.5.10 are assembled, and sealed through a high-temperature and high-pressure heat-shrink tube.

S5. The axial deformation sensor 4.5.2 and the radial deformation sensor 4.5.3 are arranged.

S6. The triaxial pressure cell 4 is provided, and the assembled fracturing test rock sample 4.5.9 is put into the triaxial pressure cell 4. A sensor line is provided, a fluid fracturing line is connected, and the conductivity and sealing of the line is checked.

S7. If there is no error, the triaxial pressure cell 4 is closed, and a bolt is tightened to fix it to the axial loading cylinder platform 1.5.

S8. The pressure cell is filled with hydraulic oil through the confining pressure loading pump 7.

S9. A temperature is applied to the rock sample through the temperature pump 6 until a target temperature for the test.

S10. A target confining pressure is applied to the pressure cell through the confining pressure loading pump 7.

S11. An axial force is applied through the axial loading system 1 until a target value, and a constant axial force is maintained.

S12. The high-energy accelerator CT scanning system 2 and the turntable system 3 are started to perform first stage scanning of the rock sample.

S13. The fracturing test is conducted on the fracturing test rock samples 4.5.9 through the fluid fracturing pump 5. When a fluid pressure reaches a certain target or a certain volume of fluid is injected, the injection is stopped. The high-energy accelerator CT scanning system 2 is started to complete second stage scanning of the fracturing test rock sample 4.5.9.

S14. The operation proceeds to the step S10, and the steps S10 and S11 are repeated until the fracturing test rock sample 4.5.9 is finally fractured and damaged.

S15. The fluid pressure and the axial force are released, the temperature of the pressure cell is reduced to room temperature, and the confining pressure of the pressure cell is released.

S16. The hydraulic oil in the triaxial pressure cell 4 returns to the confining pressure loading pump 7, and the triaxial pressure cell 4 is opened to remove the fracturing test rock sample 4.5.9 after fracturing.

S17. The fracturing test rock sample 4.5.9 after fracturing is shot and described, and test data are organized.

S18. The test is over.

As shown in FIGS. 1 to 9, a third embodiment of the present disclosure provides a multifunctional and visual rock triaxial testing method, which is based on the compression test of the multifunctional and visual rock triaxial testing system, and includes the following steps.

A1. The triaxial pressure cell 4 is removed from a middle position of the high-energy accelerator CT scanning system 2, and background CT scanning is conducted to acquire a background image.

A2. The compression test rock sample 4.5.4 is provided between the upper compression test pad 4.5.7 and the lower compression test pad 4.5.1, and sealed through a high-temperature and high-pressure heat-shrink tube.

A3. The axial deformation sensor 4.5.2 and the radial deformation sensor 4.5.3 are arranged.

A4. The triaxial pressure cell 4 is opened, and the assembled compression test rock sample 4.5.4 is put into the triaxial pressure cell 4. A sensor line is provided, and the conductivity of the line is checked.

A5. If there is no error, the triaxial pressure cell 4 is closed, and a bolt is tightened to fix it to the axial loading cylinder platform 1.5.

A6. The triaxial pressure cell 4 is filled with hydraulic oil through the confining pressure loading pump 7.

A7. A temperature is applied to the test rock sample 4.5.4 through the temperature pump 6 until a target temperature for the test.

A8. A target confining pressure is applied to the triaxial pressure cell 4 through the confining pressure loading pump 7.

A9. The high-energy accelerator CT scanning system 2 is started to perform first stage scanning of the test rock sample 4.5.4.

A10. An axial force is applied gradually through the axial loading system 1, and a stress-strain curve of the rock is recorded in real time.

A11. When the loading reaches a certain stage or a designed target stage of the test, the axial loading is stopped, and the high-energy accelerator CT scanning system 2 is started to perform second stage scanning of the rock sample.

A12. The operation proceeds to the step S10, and the steps S10 and S11 are repeated until the compression test rock sample 4.5.4 is finally compressed and damaged.

A13. The axial force is released, the temperature of the triaxial pressure cell 4 is reduced to room temperature, and the confining pressure of the triaxial pressure cell 4 is released.

A14. The hydraulic oil in the triaxial pressure cell 4 returns to the confining pressure loading pump 7, and the triaxial pressure cell 4 is opened to remove the compression test rock sample 4.5.4 after compression.

A15. The compression test rock sample 4.5.4 after compression is shot and described, and test data are organized.

A16. The test is over.

Terms such as "first" and "second" are intended to distinguish between similar objects, rather than describe or indicate a specific order or sequence.

Terms "include", "comprise" or any other variations thereof are intended to cover non-exclusive inclusions, so that a process, a method, an article, or a device/apparatus including a series of elements not only includes those elements, but also includes other elements that are not explicitly listed, or also includes inherent elements of the process, the method, the article or the device/apparatus.

The technical solutions of the present disclosure are described in the preferred implementations with reference to the drawings. Those skilled in the art should easily understand that the protection scope of the present disclosure is apparently not limited to these specific implementations. Those skilled in the art can make equivalent changes or substitutions to the relevant technical features without departing from the principles of the present disclosure, and the technical solutions derived by making these changes or substitutions should fall within the protection scope of the present disclosure.

What is claimed is:

1. A multifunctional and visual rock triaxial testing system, comprising an axial loading system, a high-energy accelerator computerized tomography (CT) scanning system, a turntable system, a triaxial pressure cell, a fluid fracturing pump, a temperature pump, a confining pressure loading pump, a power oil source, and an integrated control console, wherein the axial loading system is fixed to a ground and configured to provide an axial stress for rock compression and fracturing tests; the high-energy accelerator CT scanning system is provided inside the axial loading system and configured to perform real-time scanning on an internal structure of a rock; the turntable system is provided between the axial loading system and the high-energy accelerator CT scanning system and rotationally connected to the high-energy accelerator CT scanning system; and the triaxial pressure cell is provided inside the high-energy accelerator CT scanning system and configured to simulate a true formation temperature, stress, and fluid environment where the rock is located;

the fluid fracturing pump is fixed to the ground, connected to the triaxial pressure cell, and configured to conduct a fluid fracturing test; the temperature pump is fixed to the ground, connected to the triaxial pressure cell, and configured to provide a true temperature field for the rock; the confining pressure loading pump is fixed to the ground and configured to provide a true stress field for the rock; the power oil source is fixed to the ground and configured to provide power for the axial loading system, the confining pressure loading pump, and the fluid fracturing pump; and the integrated control console is configured to control the axial loading system, the high-energy accelerator CT scanning system, the turntable system, the triaxial pressure cell, the fluid fracturing pump, the temperature pump, the confining pressure loading pump, and the power oil source, and acquire data in real time;

the axial loading system comprises a reaction frame, an axial loading cylinder body, an axial loading cylinder connecting flange, an axial loading cylinder piston, and an axial loading cylinder platform;

the reaction frame is fixed to the ground and the axial loading cylinder body; the axial loading cylinder piston is located in the axial loading cylinder body and moves along the axial loading cylinder body; the axial loading cylinder piston is connected to the axial loading cylinder body through the axial loading cylinder connecting flange in a moving and sealed manner; the axial loading cylinder piston is fixed to the axial loading cylinder platform; and the axial loading cylinder platform is fixed to the triaxial pressure cell;

the high-energy accelerator CT scanning system comprises a detector bracket, a detector lifting system, a detector, a radiation source bracket, a radiation source lifting system, a radiation source, and a CT line assembly;

the detector bracket is connected to the turntable system and fixed to the detector lifting system; the detector lifting system is fixed to the detector; and the detector is configured to image the internal structure of the rock;

the radiation source bracket is connected to the turntable system and fixed to the radiation source lifting system; the radiation source lifting system is fixed to the radiation source; and the radiation source is configured to emit an X-ray to the rock;

the CT line assembly is connected to the turntable system and configured to control the high-energy accelerator CT scanning system;

the turntable system comprises a turntable rotor, a turntable stator, and a rotating tow;

the turntable rotor is fixed to the detector bracket, the radiation source bracket, and the CT line assembly; the turntable rotor is connected to the turntable stator through a bearing; and the turntable stator is fixed to the reaction frame;

one end of the rotating tow is fixed to the turntable rotor, and the rotating tow is allowed to coil around the turntable stator; the CT line assembly is located in the rotating tow; and the rotating tow is configured to pull the CT line assembly;

the triaxial pressure cell comprises a pressure cell base, a pressure cell cylinder body, a pressure cell end cap, a pressure cell piston, a rock sample assembly device, a high-low temperature heat exchange tube, a built-in pressure sensor, and a ball-and-socket device;

the pressure cell base is detachably fixed to the axial loading cylinder platform and fixed to a lower surface of the pressure cell cylinder body; the pressure cell cylinder body is provided therein with the rock sample assembly device; and a lower surface of the rock sample assembly device is fixed to the pressure cell base;

the high-low temperature heat exchange tube is located between the rock sample assembly device and an inner surface of the pressure cell cylinder body; and the high-low temperature heat exchange tube is fixed to the inner surface of the pressure cell cylinder body and rigidly connected to the temperature pump through a through-hole in the pressure cell base;

an upper surface of the rock sample assembly device is fixed to the ball-and-socket device; the ball-and-socket device is fixed to the built-in pressure sensor; the built-in pressure sensor is fixed to the pressure cell piston; the pressure cell piston is movable along an inner surface of the pressure cell end cap; the pressure cell end cap is fixed to an upper surface of the pressure cell cylinder body; and the pressure cell piston is fixed to the reaction frame;

the rock sample assembly device comprises a lower compression test pad, an axial deformation sensor, a radial deformation sensor, a compression test rock sample, an axial deformation cone, a contact bolt, and an upper compression test pad;

the lower compression test pad is fixed to the pressure cell base and the axial deformation sensor; the axial deformation sensor is butted with the axial deformation cone; the axial deformation cone is fixed to the upper compression test pad; the upper compression test pad is connected to the ball-and-socket device; and the compression test rock sample is located in the axial deformation sensor and butted with the axial deformation cone; and the lower compression test pad is fixed to the radial deformation sensor; the radial deformation sensor is fixed to the contact bolt; and the contact bolt is butted with the compression test rock sample.

2. The multifunctional and visual rock triaxial testing system according to claim 1, wherein the rock sample assembly device comprises the axial deformation sensor, the radial deformation sensor, the axial deformation cone, the contact bolt, a lower fracturing test pad, a fracturing test rock sample, and an upper fracturing test pad;

the lower fracturing test pad is fixed to the pressure cell base and the axial deformation sensor; the axial deformation sensor is butted with the axial deformation cone; the axial deformation cone is fixed to the upper fracturing test pad; the upper fracturing test pad is connected to the ball-and-socket device; and the fracturing test rock sample is located in the axial deformation sensor and butted with the axial deformation cone;

the lower fracturing test pad is fixed to the radial deformation sensor; the radial deformation sensor is fixed to the contact bolt; and the contact bolt is butted with the fracturing test rock sample; and a center of the lower fracturing test pad is provided with a fluid injection hole and rigidly connected to the fluid fracturing pump through a hole in the pressure cell base.

3. The multifunctional and visual rock triaxial testing system according to claim 1, wherein the axial deformation sensor and the radial deformation sensor are provided with an elastic rod structure and measure a deformation by a strain gauge on an elastic rod.

4. The multifunctional and visual rock triaxial testing system according to claim 3, wherein the reaction frame is configured to carry a reaction force during axial loading.

5. The multifunctional and visual rock triaxial testing system according to claim 4, wherein the CT line assembly comprises CT electrical, optical, and control signals.

6. The multifunctional and visual rock triaxial testing system according to claim 2, wherein the axial deformation sensor and the radial deformation sensor are provided with an elastic rod structure and measure a deformation by a strain gauge on an elastic rod.

7. The multifunctional and visual rock triaxial testing system according to claim 6, wherein the reaction frame is configured to carry a reaction force during axial loading.

8. The multifunctional and visual rock triaxial testing system according to claim 7, wherein the CT line assembly comprises CT electrical, optical, and control signals.

* * * * *